United States Patent
Smith et al.

[11] Patent Number: 6,149,590
[45] Date of Patent: Nov. 21, 2000

[54] SYSTEM FOR IDENTIFYING PREMATURE RUPTURE OF MEMBRANE DURING PREGNANCY

[76] Inventors: Ramada S. Smith, 34153 Lyncroft Ct., Farmington Hills, Mich. 48331; Brian A. Torok, 960 W. 11 Mile Rd., Berkley, Mich. 48072

[21] Appl. No.: 09/351,875

[22] Filed: Jul. 13, 1999

Related U.S. Application Data

[63] Continuation-in-part of application No. 09/120,829, Jul. 22, 1998.
[51] Int. Cl.[7] ........................................... A61B 5/00
[52] U.S. Cl. ........................ 600/367; 600/573; 600/584
[58] Field of Search .................... 606/309, 367, 606/573, 584; 604/358, 362

[56] References Cited

U.S. PATENT DOCUMENTS

| | | | |
|---|---|---|---|
| 5,063,930 | 11/1991 | Nucci | 600/367 X |
| 5,823,953 | 10/1998 | Roskin et al. | 600/367 |
| 5,823,954 | 10/1998 | Chaffringeon | 600/367 |
| 6,042,543 | 3/2000 | Warwick et al. | 600/367 X |

Primary Examiner—Cary O'Connor
Assistant Examiner—Ryan Carter
Attorney, Agent, or Firm—Harness, Dickey & Pierce, P.L.C.

[57] ABSTRACT

An article for the identification of the premature rupture of a membrane during pregnancy is disclosed. In its preferred embodiment, the article comprises a pad having an upper outer layer, a lower outer layer, and an intermediate pH-responsive component. A double-sided adhesive strip is attached to the lower outer layer. The upper outer layer is composed of a liquid permeable material. Intermediate of the upper out layer and the inner outer layer is a pH-sensitive component. This intermediate layer is a pH-sensitive material and may be one of a variety of such materials, although a preferred material is nitrazine paper. In the presence of an alkaline fluid, such as amniotic fluid, the pH-sensitive material responds by turning to a purple-blue color. The change in color acts as a visual indicator to the wearer of the possible presence of amniotic fluid outside of the amniotic sac. As an alternate embodiment, the article may be fitted with a slide for gathering amniotic fluid, thus allowing the examining physician to make a visual evaluation.

21 Claims, 3 Drawing Sheets

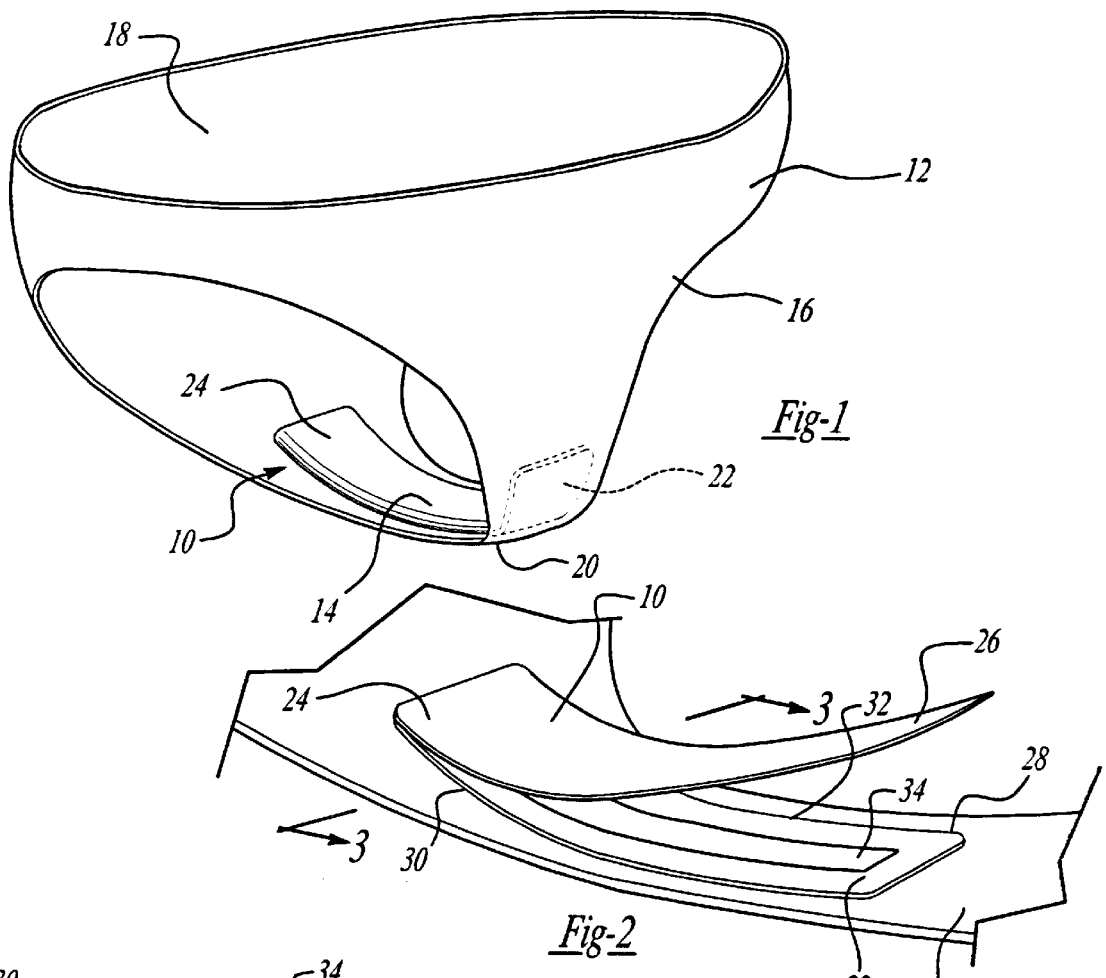
Fig-1
Fig-2
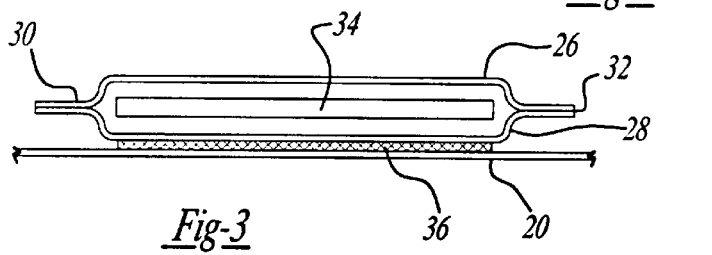
Fig-3
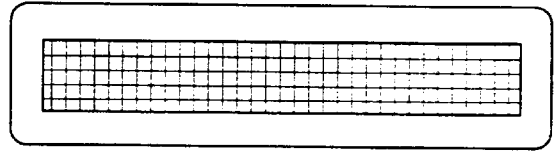
Fig-4
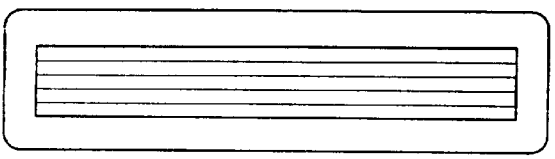
Fig-5
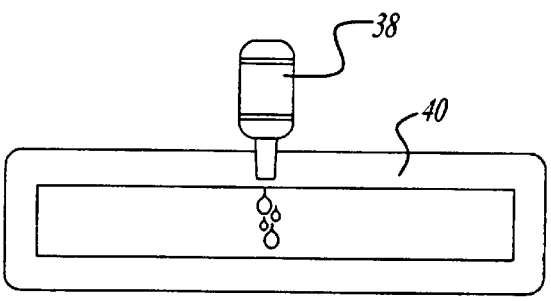
Fig-6

SYSTEM FOR IDENTIFYING PREMATURE RUPTURE OF MEMBRANE DURING PREGNANCY

CROSS-REFERENCE TO RELATED APPLICATION

This application is a continuation-in-part of U.S. patent application Ser. No. 09/120,829, filed Jul. 22, 1998, now pending.

TECHNICAL FIELD

The present invention is generally directed to an article for the identification of the premature rupture of a membrane during pregnancy. More particularly, the present invention is directed to an indicating article in the form of a multilayered pad that is fitted to the undergarment of a user. The multilayered pad includes a treated component which responds to the presence of amniotic fluid as a discharge. As an alternate embodiment, a thin flexible plastic slide may be incorporated with the pad for microscopic examination.

BACKGROUND ART

The amnion develops around the embryo during the second week following fertilization. This is the second membrane to appear after the placenta forms around the chorion. The margin of the amnion is attached to the periphery of the embryonic disk. Eventually, as the embryo grows, the amnion fuses with the chorion surrounding it, and the two membranes become a single amniochorionic membrane. Amniotic fluid fills the amniochorionic membrane to provide a watery environment to protect the growing embryo.

Ordinarily the amniochorionic membrane acts as a primary barrier to bacteria and other potentially damaging organisms by providing a protected, substantially sealed environment throughout the development of the embryo until it ruptures subsequent to the onset of labor. However, this environment is occasionally compromised when it is prematurely ruptured prior to the onset of labor. Technically, premature rupture of the membrane can occur at any time during the forty weeks of gestation. Although definitions vary, "premature rupture of the membrane" refers to rupture of the amniochorionic membrane prior to the onset of labor at any time. In either case, a ruptured membrane poses a considerable risk of infection to both mother and fetus.

Occasionally, rupturing of the membrane follows invasive techniques such as amniocentesis and may lead to infection of the developing fetus. This rupture occurs in about 1 out of every 200 procedures. For women undergoing an amniocentesis in the second trimester, detection of a rupture of the membrane is critical. A gross rupture of fluid could be potentially catastrophic for the developing fetus, as adequate amniotic fluid is a necessity to assure proper lung development, especially prior to 23 weeks.

Beyond the obvious compromise of the membrane caused by amniocentesis, the exact cause of premature rupture is not known. Possible causes include infection, cervical incompetence, and decreased strength of the membrane. Regardless of the cause, with the premature rupture of the membrane, the fetus must be promptly delivered when the mother becomes clinically infected or the fetus shows signs of potential compromise. In either situation, if left untreated, possible death to the fetus and the mother could result. It is noteworthy that chorioamnionitis is present in about 5 to 10 percent of all deliveries and, significantly, is the reason for about 10 percent of all perinatal deaths.

In the event of premature rupture of the membrane, the timing for the delivery of the baby becomes critical, as the risk of intrauterine infection increases significantly as more time passes following rupture. Accordingly, it becomes critical to provide a method of early detection of rupture. The problem is that leaking amniotic fluid—the telltale sign of rupture—is frequently confused by the mother with her own urine or vaginal discharge. (The leakage of urine during pregnancy [particularly during the latter stages] is frequently due to increased pressure on the bladder, thus adding to the overall incidence of false positives.) This results in many false alarms and unnecessary trips to either the doctor's office or to the hospital for evaluation of the pregnant woman to rule out possible rupture of the membrane. These trips lead to wasted time and energy on the part of both the patient and the physician as well as considerable expense to the health care system. A hospital audit revealed an average cost of $250.00 per visit to rule out rupture of the membrane.

Once the pregnant woman identifies leakage, today she has no practical choice but to visit her physician. Because the presence of leaking urine is fleeting, the attending physician must undertake one or more tests in the office to determine whether or not there has been a rupture of the membrane. The conventional test is for the physician to observe the cervix after employing a speculum in an effort to identify pooling of fluid behind the cervix. The physician then applies a swab of pH paper held by a forceps to the fluid located in the area of the cervix to determine whether or not amniotic fluid is present by observing a change in color. Amniotic fluid is alkaline and the pH paper reacts to its presence by turning purple-blue. In addition, the physician may examine a slide on which fluid from the posterior portion of the vagina has been placed and allowed to dry. Amniotic fluid has a very characteristic appearance when dry, called "ferning", and, when the pattern is present, can rule in the rupture of membranes. This determination can assist the physician greatly in evaluating the patient. While functional, experience shows that this examination is far more often than not unnecessary, as the etiology of the fluid is typically due to a cause other than ruptured membranes, i.e., urine, physiologic discharge, etc. The known test is also impractical, leading to particular discomfort for the patient and lost time for the physician.

A variety of in-office or in-hospital tests for the presence of amniotic fluid are known. For example, in U.S. Pat. No. 4,357,945, issued on Nov. 9, 1982 to Janko for DEVICE FOR TESTING AND RUPTURING AMNIOTIC MEMBRANE, a finger-mounted medical testing device is disclosed which tests the intactness of the amniotic membrane. The device of Janko is provided with a pH-responsive material. Upon insertion into the cervix, the indicator material is exposed to the local environment. In U.S. Pat. No. 5,425,377, issued on Jun. 20, 1995 to Caillouette for PH MEASUREMENT OF BODY FLUID, a swab is provided which includes a pH indicator for measuring the pH of vaginal moisture.

Other techniques for use in-office or in-hospital are provided in: U.S. Pat. No. 5,281,522 issued on Jan. 25, 1994 to Senyei et al. for REAGENTS AND KITS FOR DETERMINATION OF FETAL FIBRONECTIN IN A VAGINAL SAMPLE; U.S. Pat. No. 5,096,830, issued on Mar. 17, 1992 to Senyei et al. for PRETERM LABOR AND MEMBRANE RUPTURE TEST; and U.S. Pat. No. 5,554,504, issued on Sep. 10, 1996 to Rutanen for DIAGNOSTIC METHOD FOR DETECTING THE RUPTURE OF FETAL MEMBRANES.

While these various methods provide approaches to testing for amniotic fluid, they do not overcome the basic problem of requiring a professional medical technician to deal in-office or in-hospital with the administration of relevant tests. Further complicating the scenario is the fact that a ruptured amniotic membrane may lead to only a temporary leakage of amniotic fluid, with another leaking episode to occur at a later time. In the meantime, the patient may become infected, with the potential result of great injury to both the baby and the mother.

It is therefore an object of the present invention to overcome the disadvantages associated with known techniques for identifying leaking amniotic fluid and possible rupture of the amniochorionic membrane.

It is a further object of the present invention to provide an article which allows the early identification of the discharge of amniotic fluid without the necessity of a visit to a doctor's office or a hospital.

It is still another object of the present invention to provide such an article which may provide direct evidence of fluid, thus allowing the fluid to be examined microscopically which could lead to a more accurate diagnosis if presentation to a doctor's office or hospital is made.

Yet another object of the present invention is to provide such an article which may be used with minimal inconvenience to the user.

Still a further object of the present invention is to provide such an article which is worn like a sanitary napkin or pad and which may also provide the function of such sanitary items.

Finally, in these times of cost containment, the potential savings from a device which could eliminate unnecessary visits to the physician's office or to the hospital could be tremendous. Thus an additional object of the present invention is to provide such an article which can minimize false positives and have a substantial impact on and impart an economic benefit to the health care system.

SUMMARY OF THE INVENTION

The present invention achieves these objectives in an indicating device that comprises, in its preferred embodiment, a pad having an upper outer layer, a lower outer layer, and an intermediate pH-responsive layer. A double-sided adhesive strip is attached to the lower outer layer.

The upper outer layer and the lower outer layer are attached substantially the same size and are to one another along their peripheral edges. The upper outer layer and the lower outer layer are preferably composed of a non-woven material, such as a spun-bonded material, or may be composed of a webbed construction which provides the device with bulk and loft. Optionally, the lower outer layer, which comprises the lower undergarment contacting surface, is comprised of a polymerized barrier film.

The upper outer layer and the lower outer layer define substantially the same width and length. The overall size of the article may be adjusted as desired. The article may or may not be designed to achieve a high absorbency function. (While not necessarily directed to absorbency as in a menstrual pad, the article of the present invention may be configured so as to provide this added function.)

Intermediate of the upper out layer and the inner outer layer is a pH-sensitive layer. This intermediate layer is a pH-sensitive material and may be one of a variety of such materials, although a preferred material is nitrazine (yellow) paper. In the presence of an alkaline fluid, such as amniotic fluid, the pH-sensitive material responds by turning to a purple-blue color. The change in color acts as a visual indicator to the wearer. Conversely, a change to the other end of the Color Scale, such as a yellow, indicates acidity, indicating to the wearer that a normal condition is present.

Fitted to the lower outer layer is at least one fastening adhesive strip which provides an adhesive attachment means for attaching the article to the underwear of the user.

As a preferred alternate embodiment, a flexible plastic slide may be incorporated into a pad to provide evidence of amniotic fluid discharge. The slide may be removed and examined microscopically by the examining physician for evidence of amniotic discharge. The flexible slide may be incorporated with either a sheet of nitrazine paper having a plurality of fenestrations formed therein or with plural strips of nitrazine paper.

As an additional alternate embodiment of the present invention, a dropper bottle containing a pH-sensitive liquid may be provided. The liquid is selectively placed on a feminine pad and the pad is worn in its usual manner. As with the article defined above, a change in color to the purple-blue end of the Color Scale indicates that amniotic fluid may be present in the wearer's discharge.

Other objects and advantages of the present invention will be made apparent as the description progresses.

BRIEF DESCRIPTION OF THE DRAWINGS

The various advantages of the present invention will become apparent to one skilled in the art by reading the following specification and appended claims and by referencing the following drawings, in which:

FIG. 1 is a perspective view showing the manner of placing the indicating article of the present invention to an undergarment;

FIG. 2 is a perspective view of the preferred embodiment of the present invention with its upper outer layer partially peeled away from the lower outer layer to reveal the intermediate pH-sensitive layer;

FIG. 3 is a transverse cross-sectional view of the indicating article according to the preferred embodiment of the present invention taken along lines 3—3 of FIG. 2 illustrating its multilayered construction;

FIG. 4 is a top plan view of the indicating article of the present invention demonstrating to the wearer the presence of an acidic flow;

FIG. 5 is a view similar to that of FIG. 4 but demonstrating to the wearer the presence of an alkaline fluid;

FIG. 6 is a perspective view of an alternate embodiment of the present invention in the form of a pH-indicating fluid being distributed on a feminine hygiene pad;

DETAILED DESCRIPTION OF THE PREFERRED EMBODIMENTS

Figure 7:
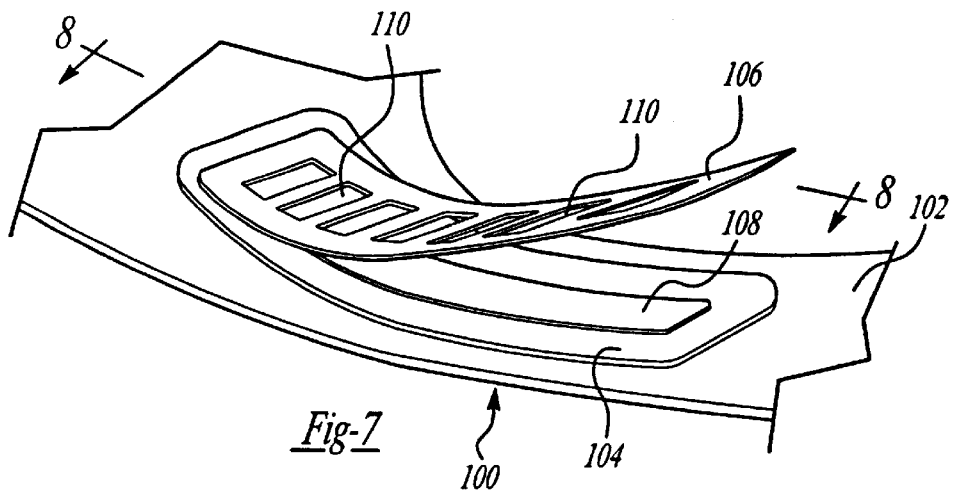
FIG. 7 is a perspective view of an additional alternate embodiment of the present invention with its upper outer layer partially peeled away from the lower outer pad layer to reveal an intermediate flexible slide.

Preferred embodiments of the indicating article of the present invention for use in an undergarment are shown throughout the figures. With respect first to FIG. 1, the article of the preferred embodiment of the present invention, generally illustrated as 10, is shown in place within an undergarment 12. The article 10 includes an elongated body 14. The undergarment is of the type commonly worn by many women and well-known as a panty. It comprises a front section 16, a back section 18, and a crotch portion 20 which joins the front and back sections 16 and 18, respectively. The article 10 is utilized by removing its release paper (shown in FIG. 3 and discussed below in relation thereto) and thereafter placing it in the undergarment 12. The elongated body 14 of the indicating article 10 is placed in the crotch portion 20 of the undergarment 12 with a first end 22 extending toward the front section 16 and a second end 24 toward the back section 18 of the undergarment 12. The lower outer layer of the article 10 is in contact with the inner surface of the center crotch portion 20 of the panty 12. The adhesive strips maintain the elongated body 14 in position.

FIG. 2 is a perspective view of the article 10. The article 10 includes an upper outer layer 26 and a lower outer layer 28. The layers 26 and 28 may be made of a non-woven material, such as a spunbonded material. Alternatively, the layers 26 and 28 may be composed of a webbed construction which provides the device with bulk and loft.

The upper outer layer 26 is preferably liquid permeable to allow body fluids to substantially pass. The upper outer layer 26 is also in contact with the wearer's skin. Accordingly, the upper outer layer 26 is preferably composed of a compliant, soft-feeling material that is non-irritating to the parts of the user's skin with which it is in contact. The upper outer layer 26 can be made from any of the materials conventional for this type of use. Non-limiting examples of suitable materials that can be used as the upper outer layer 26 are non-woven cotton, polyester, polyethylene, polypropylene, nylon and rayon and formed thermoplastic films. The preferred type of material is a spunbonded one that is pervious to liquids but is nevertheless non-absorbent. The particular material is selected so that the surface of the upper outer layer 26 remains dry and is thus more comfortable to the wearer. The recommended thickness of the upper outer layer 26 is between 1 and 2 mils with the preferred thickness being about 1 mil.

The lower outer layer 28, which comprises the lower undergarment contacting surface, may be comprised of a polymerized barrier film. In this embodiment, the lower outer layer 28 may be composed of a polyethylene film such as that offered by the Clopay Corporation (Cincinnati, Ohio) under the designation P18-0401 and by Ethyl Corporation (Terre Haute, Ind.) under the designation XP39385. The upper outer layer 26 and the lower outer layer 28 may be composed of selected materials so as to provide a mere carrier for the pH-sensitive component or may be composed of material such that the article 10 acts additionally as a sanitary napkin, capable of absorption of body fluids. In this situation, the upper outer layer 26 would still be composed of a liquid permeable material. However, the lower outer layer 28 would be entirely or partially composed of an absorbent material or an additional absorbent layer (not shown) would be added between the upper outer layer 26 and the lower outer layer 28 with the pH-sensitive component (discussed below with respect to FIG. 2) fitted adjacent the upper outer layer 26. Where absorbency is desired to allow the article 10 to double as an absorbent pad, a suitable absorbent, hydrophilic fiber intended to absorb and contain liquid may be used. Examples of suitable hydrophilic fiber material include cellulose, modified cellulose, rayon, polyesters such as polyethylene terephtalate (DACRON [trademark]), hydrophilic nylon (HYDROFIL [trademark]), and the like. The selection of the particular material is only controlled by the desired absorbent capacity of the absorbent material.

The upper outer layer 26 and the lower outer layer 28 are joined along their peripheral edges by known methods of joining, including chemical bonding and physical stitching. As used herein, the term "joined" encompasses configurations whereby an element is directly secured to the other element by affixing the element directly to the other element, configurations whereby the element is indirectly secured to the other element by affixing the element to intermediate member(s) which in turn are affixed to the other element, and configurations whereby one element is integral with another element, i.e., one element is essentially part of the other element.

The article 10 has a pair of opposed sides 30 and 32. The sides 30 and 32 are illustrated as being substantially parallel and linear, but it is to be understood that the sides 30 and 32 may be non-linear and may define any of a variety of curved lines. For example, the sides 30 and 32 may be configured so as to follow the curved, crotch area edges that define the leg holes of an undergarment.

The overall dimensions of the article 10 may be varied as necessary depending on the size and style of the undergarment and the intended use of the article 10. For example, when the user is lying in the prone position, there is a tendency for body fluid to gravitate toward either the person's front side or back side, depending on which side the person is lying. The article 10 may accordingly be longer for this purpose, and may accordingly be particularly desirable for use by those at-risk women who are substantially bed ridden during the last weeks of pregnancy. However, with the longitudinal centerline of the article 10 representing the Y-axis and the transverse centerline representing the X-axis as oriented by reference to a planar Cartesian coordinate system, the preferred size of the article 10 is between 150 and 170 mm along the Y-axis (or the long axis) of the article 10 and between 100 and 125 along the X-axis or along the width of the article 10.

The article 10 is provided with a pH-sensitive component 34. The component 34 defines a strip of a flexible material, such as a strip of nitrazine (yellow) paper, which effects a color change in response to acidity or alkalinity. The component 34 is fitted between the upper outer layer 26 and the lower outer layer 28. Accordingly, the selection of material for the upper outer layer 26 is limited only by the requirement that the material be selected from those of specific density or composure so as to permit the color of the component 34 to be visualized by the wearer by reference to the upper outer layer 26, that is, without having to disassemble the article 10 to verify the color.

While nitrazine paper is the preferred form of material for indicating pH, other pH indicators could be used as well. Such indicators may be selected from the group consisting of bromochlorophenol blue sodium salt, bromocresol green ACS, bromocresol green sodium salt ACS, bromocresol purple, bromocresol purple sodium salt, bromophenol blue ACS, bromophenol blue sodium salt ACS, bromopyrogallol red, bromothymol blue ACS, bromothymol blue sodium salt ACS, bromoxylenol blue, calcein/fluroexon, calconcarboxylic acid, calmagite, chlorophenol red, o-cresolphthalein, o-cresolphthalein complexone, o-cresolphthalein complexone disodium salt, m-cresol purple, m-cresol purple sodium salt, cresol red, cresol red sodium salt, erichrome blue black R, ethyl orange sodium salt, fast sulphone black F, litmus powder, methyl orange ACS, methyl red free acid ACS, methyl red HCL ACS, methyl red sodium salt ACS, methylthymol blue, murexide powder, P.A.N., P.A.R., patent blue VF, phenolphthalein ACS, phenolphthalein ACS, phenol red ACS, phenol red sodium salt ACS, pyrocatechol violet, pyrogallol red, quinaldine red, SPADNS, thorin, thymol blue ACS, thymol blue sodium salt ACS, thymolphtahalein ACS, tropaeolin O, and xylenol orange tetrasodium salt ACS.

FIG. 3 is a transverse cross-sectional view of the article 10 of the present invention taken along lines 3—3 of FIG. 2. This view illustrates the article 10 in place on the crotch portion 10 of the undergarment 12. The article 10 can be configured such that the upper outer layer 26 and the lower outer layer 28 are mere carriers for the pH-sensitive component 34, or may function simultaneously as a feminine napkin or pad or a panty liner or shield. A plurality of fastening adhesive strips 36 are provided on the underside of the article 10 for removable attachment to the undergarment 10. Any adhesive or glue used in the art for such purpose can be used herein, with pressure sensitive adhesives being preferred. Suitable adhesives are Century A-305-IV manufactured by the Century Adhesives Corporation and Instant Lok 34-2823 manufactured by the National Starch Company. As illustrated, a single fastening adhesive strip 36 is only of a width that is less than that of the elongated body 12 of the article 10. The adhesive strip 36 is covered with a release paper (not shown) to keep the strip 36 from sticking to extraneous surfaces prior to use. Any conveniently available release paper commonly used for such purposes can be used herein. Non-limiting examples of suitable release papers are BL 30 MG-A Silox EI/O and BL 30 MG-A Silox 4 P/O, both of which are manufactured by the Akrosit Corporation. To employ such a devise, the user would first remove a release paper and apply the article 10 with a slight pressure to the crotch area 20 of the undergarment 12.

In use, the wearer removes the release tape (not shown) to expose the adhesive strip 36 of the article 10 and places the article 10 in the crotch portion 20 of her undergarment 12. The user then wears the undergarment 12 in the usual manner, adjusting or removing them occasionally as required to observe the color status of the article 10. A yellow color of the pH-sensitive component 34 as indicated in FIG. 4 demonstrates to the wearer the presence of an acidic flow and can be safely disregarded as urine. Conversely, a visualized purple-blue color of the pH-sensitive component 34 as illustrated in FIG. 5 would demonstrate to the wearer the presence of an alkaline fluid. As noted above, the alkaline fluid may be a false positive if seminal fluid or blood. However, the only other alkaline fluid possibly present would be amniotic fluid, indicating to the wearer that there is a possible rupture of the amniotic sac, whereupon a physician should be contacted. In any event, the wearer may dispose of the article 10 after use in a manner consistent with the normal disposal of a feminine pad or napkin.

As an alternate embodiment of the present invention, a liquid form of the pH-sensitive component may be used. With reference to FIG. 6, a liquid form of the pH-sensitive component is housed in a bottle 38. The wearer (not shown) would apply a series of drops of the liquid material along the approximate mid-point of the upper, body-facing side of a pad or napkin 40. In this embodiment, the wearer would apply and use the pad or napkin 40 in a manner similar to that of the embodiment of FIGS. 1 through 5 described above.

As an alternative to the use of nitrazine paper, other means of detecting amniotic fluid may be employed. FIGS. 7 through 11 illustrate additional embodiments of the present invention which commonly employ a flexible plastic slide which may be microscopically examined for physical evidence of amniotic fluid.

With respect to FIG. 7, a perspective view of an amniotic fluid detecting article, generally shown as 100, is illustrated. The article 100 is shown in place in an undergarment 102 and is fastened in place in a manner similar to the article 10 discussed above. The article 100 includes a lower outer layer or pad body 104 which is positioned directly on the undergarment 102, an outer upper layer 106, and an intermediate layer 108.

The lower outer layer 104 may be composed of the same materials as the lower outer layer 28 described above. According to the present embodiment, the lower outer layer 104 functions to provide structure and support.

The outer upper layer 106 is preferably a single sheet of nitrazine paper. The nitrazine paper is provided for detection of amniotic fluid and thus functions along the lines of its counterpart, the pH-sensitive component 34, discussed above. While it is preferred that the layer 106 be nitrazine, this is not absolute, as other pH-sensitive materials discussed above could as well be used.

A plurality of fenestrations 110 are formed in the upper outer layer 106. The fenestrations 110 function to permit passage of fluid therethrough. The number and configuration of the fenestrations 110 may be altered as desired to meet specific needs.

The intermediate layer or slide 108 is composed of a fluid-gathering, flexible plastic slide. The slide material forming the slide 108 should be chemically and biologically inert, like glass, so as not to interfere with microscopic examination. Preferably, the slide 108 should be composed of a thin, flexible plastic.

The upper layer 106 is readily separable from the lower layer 104. This ready separation provides the examining physician with a simple method by which to generally expose the slide 108 and remove the slide 108 for examination. To accommodate the ready separation, a releasable adhesion material would be used.

Figure 8:
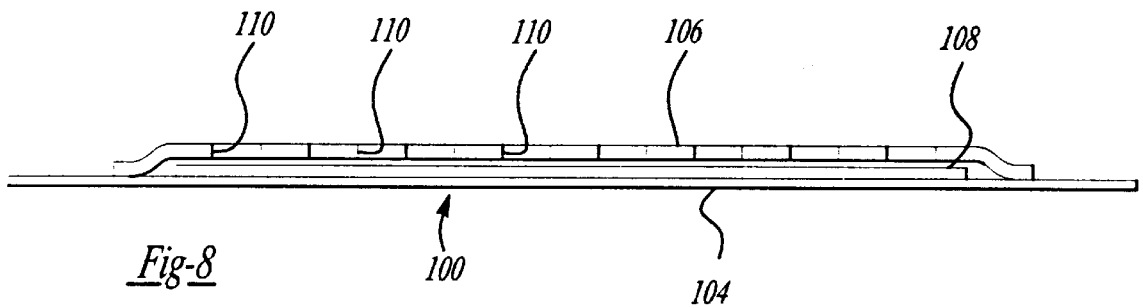
FIG. 8 is a transverse cross-sectional view of the indicating article of FIG. 7 taken along lines 8—8 of FIG. 7 illustrating its multilayered construction.

FIG. 8 is a cross-sectional view of the article 100 taken along lines 8—8 of FIG. 7. This cross-sectional view of the article 100 more clearly shows the gaps or fenestrations 110 which allow the flow-through of fluid, a portion of which gathers on the upper side of the slide 108. The slide 108 may be removed from between the upper layer 106 and the lower layer 104 for visual examination for evidence of premature amniotic rupture.

Figure 9:
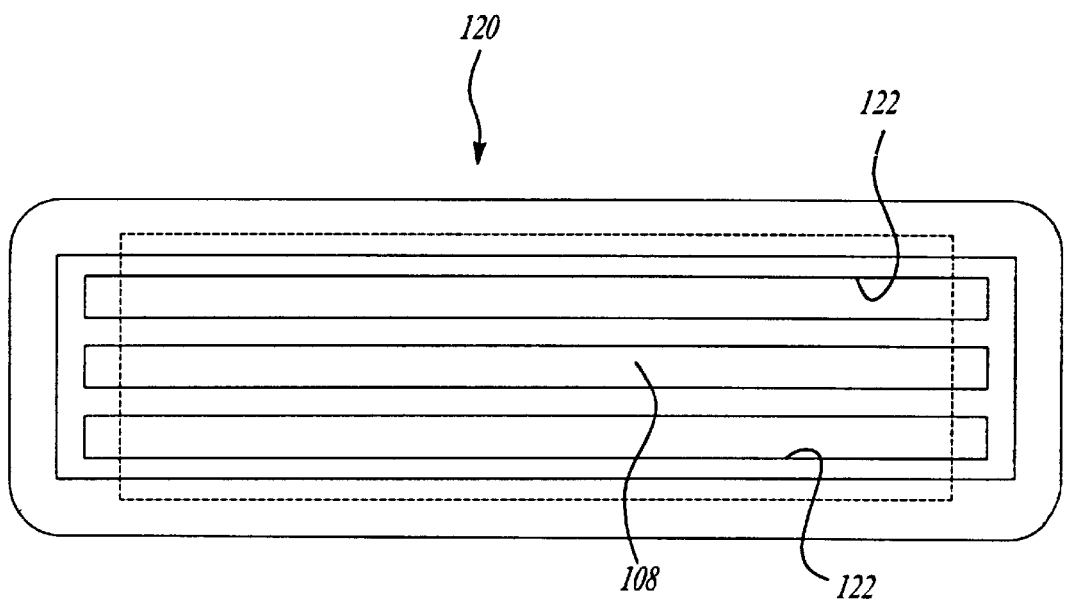
FIG. 9 is a top plan view of an indicating article according to a further alternate embodiment of the nitrazine-flexible slide combination of the present invention.

FIG. 9 discloses an article, generally illustrated as 120, which is virtually identical to the article 100 with the exception of a series of fenestrations 122 which run along the long axis of the slide 108 rather than perpendicular to it as in the case of the fenestrations 110 of the article 100.

Figure 10:
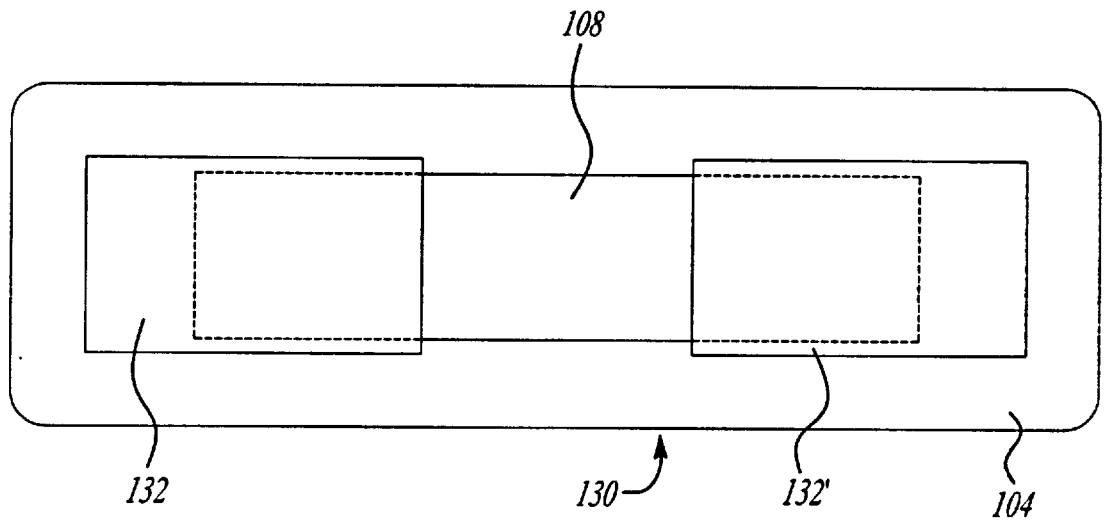
FIG. 10 is a top plan view of an indicating article according to yet another alternate embodiment of the nitrazine-flexible slide combination of the present invention.
Figure 11:
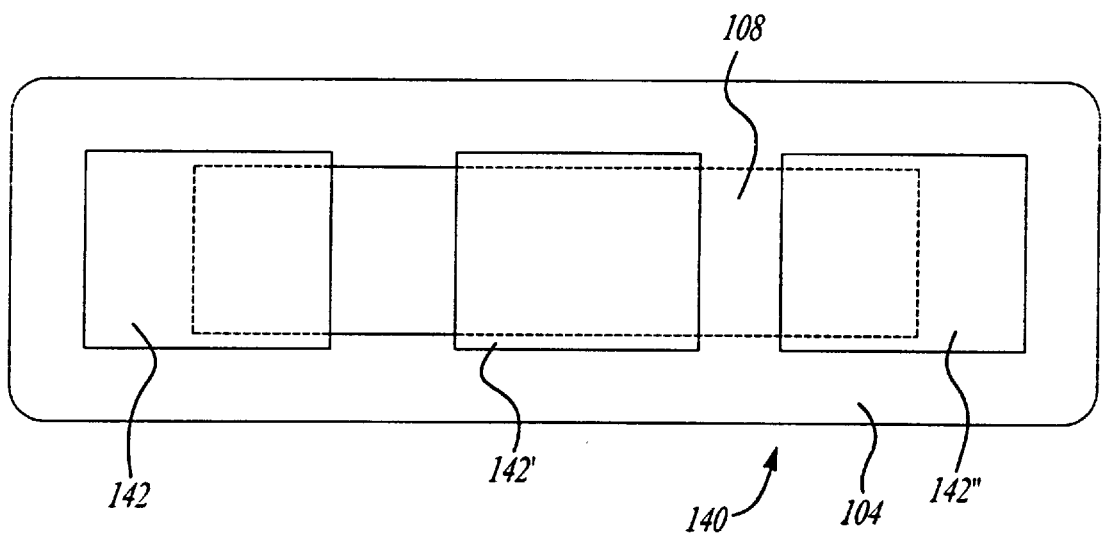
FIG. 11 is a top plan view of an indicating article according to still another alternate embodiment of the nitrazine-flexible slide combination of the present invention.

As an alternative to the formation of fenestrations in the upper layer 106, the slide 108 may be held in place against the lower layer 104 by a series of two or more strips. Such a configuration is set forth in FIGS. 10 and 11. With particular reference to FIG. 10, an article, generally illustrated as 130, is illustrated. The article 130 includes a pair of spaced-apart strips 132, 132' which are used to retain the slide 108 against the lower layer 104. Similarly, and with respect to FIG. 11, an article, generally illustrated as 140, includes three strips 142, 142', 142" which are used to hold the slide 108 in place. In both articles 130 and 140 the strips may or may not be composed of a nitrazine material.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. A system for identifying the premature rupture of a membrane during pregnancy for use with a pants of a wearer, the system comprising:
   a pad for placement in the crotch portion of the pants of the wearer, the pad including an upper layer and a lower layer; and
   a microscope-visualizable slide fitted to said pad.

2. The system for identifying the premature rupture of a membrane according to claim 1, wherein said slide is a sheet of a flexible plastic.

3. The system for identifying the premature rupture of a membrane according to claim 1, wherein said upper layer of said pad is composed of a pH-sensitive material.

4. The system for identifying the premature rupture of a membrane according to claim 3, wherein said pH-sensitive material is a sheet of nitrazine treated material.

5. The system for identifying the premature rupture of a membrane according to claim 4, wherein said nitrazine-treated material is a sheet of nitrazine paper.

6. The system for identifying the premature rupture of a membrane according to claim 1, further including at least one adhesive strip provided on said lower layer of said pad.

7. The system for identifying the premature rupture of a membrane according to claim 1, wherein said upper layer is liquid-permeable.

8. The system for identifying the premature rupture of a membrane according to claim 1, wherein said lower layer is at least partially liquid-impermeable.

9. The system for identifying the premature rupture of a membrane according to claim 1, wherein said lower layer is liquid absorbent.

10. The system for identifying the premature rupture of a membrane according to claim 1, wherein said upper layer includes a plurality of fluid-passing fenestrations.

11. The system for identifying the premature rupture of a membrane according to claim 1, wherein said upper layer defines at least two strips for holding said slide to said lower layer.

12. A pad for identifying the premature rupture of a membrane during pregnancy for use with the pants of a wearer, the pad comprising:
    an upper layer;
    an intermediate component;
    a lower layer, whereby said intermediate component is fitted between said upper and lower layers, said intermediate component being a microscope-visualizable slide.

13. The pad for identifying the premature rupture of a membrane according to claim 12, wherein said intermediate component is a sheet of a flexible plastic.

14. The pad for identifying the premature rupture of a membrane according to claim 9, wherein said pad comprises a pH-sensitive component, and wherein said pH-sensitive component is in liquid form.

15. The pad for identifying the premature rupture of a membrane according to claim 14, wherein said pH-sensitive component is nitrazine treated material.

16. The pad for identifying the premature rupture of a membrane according to claim 15, wherein said nitrazine-treated material is a sheet of nitrazine paper.

17. The pad for identifying the premature rupture of a membrane according to claim 12, further including at least one adhesive strip provided on said lower layer.

18. The pad for identifying the premature rupture of a membrane according to claim 12, wherein said upper layer is liquid-permeable.

19. The pad for identifying the premature rupture of a membrane according to claim 12, wherein said lower layer is at least partially liquid-impermeable.

20. The pad for identifying the premature rupture of a membrane according to claim 12, wherein said lower layer is liquid absorbent.

21. A method for identifying the premature rupture of a membrane during pregnancy, the method comprising the steps of:
    forming a pad for use in the pants of a wearer;
    fitting said pad with a microscope-visualizable slide;
    wearing said pad with said slide for a select period of time; and
    visualizing said slide to determine the physical presence of material which would indicate said premature rupture.

* * * * *